United States Patent [19]

Correia et al.

[11] Patent Number: 4,954,231

[45] Date of Patent: Sep. 4, 1990

[54] FUNCTIONAL CHLOROFLUORO COMPOUNDS AND THEIR PREPARATION

[75] Inventors: Yves Correia, Chateau-Arnoux; Gilles Drivon, Saint-Martien en Haut; Jean Lesparre, Volonne, all of France

[73] Assignee: Societe Atochem, Puteaux, France

[21] Appl. No.: 452,339

[22] Filed: Dec. 19, 1989

[30] Foreign Application Priority Data

Dec. 27, 1988 [FR] France .................. 88 17241

[51] Int. Cl.$^5$ ............................................. C07C 69/00
[52] U.S. Cl. .................................. 204/157.6; 558/283
[58] Field of Search .................... 558/283; 204/157.6

[56] References Cited

U.S. PATENT DOCUMENTS 3,047,610  7/1962  Brace et al. .................. 558/260
3,325,540  6/1967  Anello et al. ................. 562/840

FOREIGN PATENT DOCUMENTS 0157739  10/1985  European Pat. Off. ........... 558/283

*Primary Examiner*—John F. Niebling
*Assistant Examiner*—Isabelle Rodriguez

*Attorney, Agent, or Firm*—Stevens, Davis, Miller & Mosher

[57] ABSTRACT

The subject of the invention is functional chlorofluoro compounds of general formula:

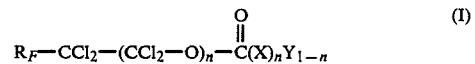

$$R_F-CCl_2-(CCl_2-O)_n-\overset{O}{\underset{\|}{C}}(X)_n Y_{1-n} \quad (I)$$

in which $R_F$ denotes a perfluoroalkyl radical, n is equal to 0 or 1, X denotes a chlorine or fluorine atom or a trichloromethyl or trifluoromethyl radical, and Y denotes a chlorine atom, an optionally salified or esterified hydroxyl group or an optionally substituted amino group, the arrangement $R_F-CCl_2-(CCl_2-O)_n$ containing at least 3 carbon atoms.

By photochlorination of the esters $R_F-CH_2CH_2-O-CO-X$, the compounds I (n=1) are obtained, which are then rearranged to acid chlorides I (n=0, Y=Cl) from which the corresponding acids, salts, esters and amides are optionally formed (formula I with n=0 and Y=optionally salified or esterified hydroxyl or optionally substituted amino).

11 Claims, No Drawings

FUNCTIONAL CHLOROFLUORO COMPOUNDS AND THEIR PREPARATION

FIELD OF THE INVENTION

The present invention relates to the field of polyhalogenated organic compounds, and relates more especially to functional chlorofluoro compounds in which a perfluorinated radical is joined to an acidic functional group or derivative (halide, ester, amide) via one or two —CCl$_2$— bridges.

BACKGROUND OF THE INVENTION

Many polyfluorocarboxylic acids, in particular perfluoroalkanecarboxylic acids and 2-(perfluoroalkyl)ethanecarboxylic acids, are already known. These acids and their derivatives have found many uses, for example as wetting agents or surfactants or as intermediates for the preparation of agents for the treatment of textiles, leather or paper.

Chlorofluorocarboxylic acids are also known. But, in most cases, the chlorine and the fluorine are bound to the same carbon atoms as, for example, in the acids Cl(CF$_2$CFCl)$_n$—COOH described by R. N. Haszeldine, J. Chem. Soc., 4291-4302 (1955), or a —CCl$_2$— bridge interrupts the perfluorinated chain, as, for example, in the acid CF$_3$—CCl$_2$—CF$_2$—COOH described by B. Boutevin et al., Eur. Polym. J., 12(5), 283-8 (1976).

However, only a few compounds are at present known in which the acidic functional group is linked to a perfluoro radical via a —CCl$_2$— bridge. These compounds are, more specifically, 2,2-dichloro-3,3,3-trifluoropropionic acid, its chloride and its alkyl esters, J. D. Park et al, J. Org. Chem., 21, 220-2 (1956), prepared from 2,2-dichloro-3,3,3-trifluoropropenyl ethyl ether. The fluoride of this acid, which is usable for the preparation of surfactants, impregnating agents or herbicides, has also been described in German Patent No. 1,900,758 where it is prepared by the action of sodium fluoride or potassium fluoride on hexachloroacetone.

The preceding references are hereby incorporated by reference.

DETAILED DESCRIPTION OF THE INVENTION

The subject of the present invention is now a new series of functional chlorofluoro compounds in which the acidic functional group is linked to a perfluoro radical via one or two —CCl$_2$— bridges.

The new compounds according to the invention may be represented by the general formula:

$$R_f\text{—}CCl_2\text{—}(CCl_2\text{—}O)_n\text{—}\overset{\overset{O}{\|}}{C}(X)_nY_{1-n} \quad (I)$$

in which R$_f$ denotes a perfluoroalkyl radical, n is equal to 0 or 1, X denotes a chlorine or fluorine atom or a trichloromethyl or trifluoromethyl radical, and Y denotes a chlorine atom, an optionally salified or esterified hydroxyl group or an optionally mono- or di-substituted amino group. The arrangement R$_f$—CCl$_2$—(CCl$_2$—O)$_n$ contains at least 3 carbon atoms.

The perfluoroalkyl radical R$_f$ can be linear or branched and can contain from 1 to 20 carbon atoms. Preferably, it is a linear radical containing from 2 to 12 carbon atoms.

When Y denotes a salified hydroxyl group, the cation can be inorganic (alkali metal, ammonium) or organic (primary, secondary or tertiary amine salt) in nature.

When Y is an esterified hydroxyl group, the alcohohol radical is advantageously that of a primary, secondary or tertiary aliphatic or cycloaliphatic alcohol. Alcohols containing from 1 to 12 carbon atoms, such as, for example, methanol, ethanol, 2-ethylhexanol, dodecanol and cyclohexanol are preferred.

When Y is an amino group, the latter can be substituted with alkyl radicals (preferably C$_1$ to C$_{12}$ alkyl), cycloalkyl radicals (for example cyclohexyl), aromatic radicals (for example phenyl, optionally substituted with one or more halogen atoms, alkyl radicals or nitro groups) or heterocyclic radicals.

The compounds according to the invention are prepared according to methods that are known per se, from the esters of formula:

$$R_F\text{—}CH_2CH_2\text{—}O\overset{\overset{}{}}{C}\text{—}X \quad (II)$$
$$\|$$
$$O$$

in which R$_F$ and X have the same meaning as above. These esters are, for the most part, known products which, generally speaking, may be obtained by reacting a 1,1,2,2tetrahydroperfluoroalkanol R$_F$—CH$_2$CH$_2$OH with an acid halide Hal—CO—X such as phosgene, carbonyl fluoride, trifluoroacetyl chloride and, preferably, trichloroacetyl chloride. Another access route to the esters (II) in which X is CCl$_3$ consists in subjecting a mixture of 2-(perfluoroalkyl)ethyl iodide R$_f$—CH$_2$CH$_2$I, trichloroacetic acid and sulphuric acid to the action of hydrogen peroxide at a temperature of 60° to 90° C.

By photochlorination of the esters of formula (II), the compounds I-a (formula I with n=1) are obtained, according to the reaction:

$$R_F\text{—}CH_2CH_2\text{—}O\overset{\overset{}{}}{C}\text{—}X + 4Cl_2 \xrightarrow{h\nu} \quad (I\text{-}a)$$
$$\|$$
$$O$$

$$R_F\text{—}CCl_2\text{—}CCl_2\text{—}O\overset{\overset{}{}}{C}\text{—}X + 4HCl$$
$$\|$$
$$O$$

This photochlorination may be performed at a temperature of between 50° and 200° C., and preferably between 80° and 170° C., with any light source capable of exciting the chlorine atom, that is to say emitting in the blue, for example low or high pressure mercury vapor lamps. The operation can be performed in the presence or absence of a solvent which is inert for chlorine, for example, carbon tetrachloride, the chlorobenzenes (in particular dichloro- and trichlorobenzenes) or trichloroacetyl chloride. It is possible for the volume of solvent to range up to ten times that of the starting compound (II). Although it is possible to work under pressure (up to 5 bars), the photochlorination is usually performed at atmospheric pressure or, better, under slightly reduced pressure. The gaseous chlorine, which must contain less than 1000 ppm of oxygen, but may be diluted with an inert gas such as nitrogen, is introduced continuously into the reaction medium in a quantity which can vary within wide limits but is generally between the theoretical quantity (4 moles) and 10 times this theoretical quantity. The progess of the photochlorination can be followed by assaying the hydrochloric acid liberated.

The compounds (I-a) can, if so desired, be isolated by vacuum distillation of the reaction mixture, and optionally purified by recrystallization in an inert solvent such as, for example, hexane.

By rearrangement of the compounds I-a (isolated or otherwise), access is then gained to the acid chlorides I-b (formula I with n=0 and Y=Cl), according to the reaction:

$$R_F-CCl_2-\underset{\underset{Cl}{|}}{\overset{\overset{Cl}{|}}{C}}-O-\underset{\underset{O}{\|}}{C}-X \longrightarrow$$

(I-a)

$$R_F-CCl_2-\underset{\underset{O}{\|}}{C}-Cl + X-CO-Cl$$

(I-b)

This rearrangement is generally accomplished by heating to a temperature ranging from 60° to 140° C., and preferably between 80° and 120° C. To speed up the operation, a tertiary amine or a salt (in particular a hydrohalide) of such an amine can be used as a catalyst, in a quantity which can reach 5% relative to the weight of compound I-a, and is preferably between 0.1 and 1%. According to a preferred procedure, this rearrangement can be carried out without isolation of the compound I-a directly on the reaction mixture derived from the photochlorination stage, on condition, however, if this stage has been performed in the presence of a light solvent, of removing the latter beforehand by vacuum distillation.

The acid chlorides I-b and X—CO—Cl formed may be separated by fractional distillation. The acid chloride X—CO—Cl recovered can be reused for the synthesis of the starting esters (II).

From the compounds I-b, the other compounds according to the invention (formula I with n=0 and Y=optionally salified or esterified OH group or optionally substituted amino group) are obtained by the traditional methods of saponification, salification, esterification and amidation.

The compounds according to the invention may be used in many fields, especially as intermediates for making known perfluorinated carboxylic acids by fluorination, or, in particular in the form of lithium salts, as surfactants, in the usual applications of fluorinated surfactants, for example for the polymerization of certain fluorinated monomers.

EXAMPLES

The examples which follow illustrate the invention without limiting the latter. The percentages stated are understood to be by weight except where otherwise stated. The solvent used for the NMR spectra is deuterated chloroform $CDCl_3$.

EXAMPLE 1

47.8 g (0.263 mole) of trichloroacetyl chloride were added in the course of half an hour at 30° C. to 95.6 g (0.263 mole) of tridecafluorooctanol $C_6F_{13}CH_2CH_2OH$. After the mixture was heated to 60° C. for 1 hour, the hydrochloric acid formed was removed with a stream of nitrogen at 20° C.

The tridecafluorooctyl trichloroacetate thereby obtained was then chlorinated under UV radiation and at a temperature of 80° to 130° C. by means of a stream of chlorine at a flow rate of approximately 0.3 mole/hour until the theoretical quantity of hydrochloric acid was liberated (approximately 17 hours).

The mixture obtained (164 g) was then distilled under vacuum, and the following fractions were collected successively:

1st fraction (≦20° C. at 1467 Pa): 20.4 g of trichloroacetyl chloride
 2nd fraction (60° to 68° C. at 1467 Pa): 56 g of crude $C_6F_{13}CCl_2COCl$ (total chlorine: 20.4%)
 3rd fraction (151° C. at 1067 Pa): 80.5 g of $C_6F_{13}CCl_2CCl_2OCOCCl_3$ (total chlorine: 38.1%)
 residue: 7.1 g.

After recrystallization of the 3rd fraction in hexane, a white solid of melting point equal to 59° C. was obtained, the $^{13}C$ NMR spectrum of which is as follows:

$$CF_3(CF_2)_5-CCl_2-CCl_2-O-\overset{\overset{O}{\|}}{C}-CCl_3$$

δ (ppm) ........... 89.9         154.8  88.3

EXAMPLE 2

75 g of trichloroacetyl chloride were added in the course of half an hour at 45° C. to 96.2 g (0.207 mole) of heptadecafluorodecanol $C_8F_{17}CH_2CH_2OH$. The mixture is then heated to 60° C. for one hour.

After the hydrochloric acid was driven off with a stream of nitrogen at 20° C., the heptadecafluorodecyl trichloroacetate was chlorinated at between 60° and 128° C. under UV radiation with a stream of chlorine at a flow rate of approximately 0.35 mole/hour, until the theoretical quantity of hydrochloric acid had been substantially collected (approximately 20 hours).

The mixture was then distilled under vacuum, and the following were successively obtained:

a first fraction (<92° C. at 1333 Pa) consisting predominantly of trichloroacetyl chloride
 a second fraction (92° C. at 1333 Pa) weighing 77.8 g and consisting of 2,2-(dichloro)heptadecafluorodecanoyl chloride $C_8F_{17}CCl_2COCl$ (total chlorine: 18.8%)
 a residue weighing 31 g and having a chlorine content of 27.7%.

By recrystallization of this residue in hexane, 1,1,2,2-(tetrachloro)heptadecafluorodecyl trichloroacetate $C_8F_{17}CCl_2CCl_2OCOCCl_3$ was obtained, which takes the form of a white solid of melting point equal to 62° C. (chlorine content: 32.3%).

EXAMPLE 3 a/ Synthesis of 2,2-(dichloro)tridecafluorooctanoyl chloride 109.2 g (0.3 mole) of tridecafluorooctanol $C_6F_{13}CH_2CH_2OH$ are placed in a reactor equipped with a stirrer, a gas inlet, a dropping funnel, a condenser connected to a waterscrubbing column and a device for illumination with a blue lamp. The temperature is brought to 60° C. 54.6 g (0.3 mole) of trichloroacetyl chloride are run in, taking 15 minutes, while the reaction is swept with nitrogen. 0.29 mole of hydrochloric acid is collected in the gas.

A stream of chlorine (flow rate: 0.4 mole/hour) is then introduced under illumination while the temperature is raised to 130°–140° C. and the $Cl^-$ ions liberated are collected. When about 1.2 mole of $Cl^-$ have been collected, the mixture is stripped with a stream of nitrogen. 1 g of triethylamine hydrochloride is then added. The mixture is heated to 100° C. for 2 hours.

By distillation under vacuum (2533 Pa), trichloroacetyl chloride is first obtained, followed at between 83° and 85° C. by 100 g of 2,2-(dichloro)tridecafluorooctanoyl chloride $C_6F_{13}CCl_2COCl$ (yield: 71.6%), identified by the following characteristics:

Electron impact (ei) mass spectrum with isotope Cl=35: molecular mass=464

$^{13}C$ NMR:

$\delta$ CO=162.6 ppm $\delta$ $CCl_2$=83.7 ppm $^{19}F$ NMR spectrum for: $CF_3$—$CF_2$—$CF_2$—$CF_2$—$CF_2$—$CF_2$—$CCl_2$—$COCl$ $\delta$(ppm)=0 45.1 41.4 40.9 33.1 25.5 b/ 2,2-(dichloro)tridecafluorooctanoic acid $C_6F_{13}CCl_2COOH$

This acid, obtained by hydrolysis of 2,2-(dichloro)-tridecafluorooctanoyl chloride was identified by electron impact (ei) mass spectrometry with the isotope Cl=35: molecular mass=446.

c/ 2,2-(dichloro)tridecafluorooctanoic acid methyl ester

By reacting the above acid with excess methanol, the corresponding methyl ester $C_6F_{13}CCl_2COOCH_3$ was obtained, identified by the following characteristics:

electron impact mass spectrometry: molecular mass=460

$^1H$ NMR spectrum (reference TMS): $\delta$=3.97 ppm $^{19}F$ NMR spectrum for: $CF_3$—$CF_2$—$CF_2$—$CF_2$—$CF_2$—$CF_2$—$CCl_2$—$COOCH_3$ $\delta$(ppm)=0 45.3 41.5 41.0 34.7 27.4 d/ N-(n-butyl)-2,2-(dichloro)tridecafluorooctanamide

By reacting 2,2-(dichloro)tridecafluorooctanoyl chloride with n-butylamine, N-(n-butyl)-2,2-(dichloro)-tridecafluorooctanamide $C_6F_{13}CCCl_2CONH(CH_2)_3CH_3$ was obtained. The IR spectrum of which is in agreement (CO band at 1695 $cm^{-1}$; NH bands at 1520 and 3350 $cm^{-1}$; CF band at 1200–1250 $cm^{-1}$).

e/ Lithium 2,2-(dichloro)tridecafluorooctanoate

A solution of 2.78 g of Lithium hydroxide (LiOH.$H_2O$) in 10 g of water is added to 15.4 g of 2,2(dichloro)-tridecafluorooctanoyl chloride. The mixture is then diluted with water to a weight of approximately 150 g. A solution is thereby obtained containing approximately 10% of Lithium 2,2-(dichloro)tridecafluorooctanoate. The measurement of the critical micellar concentration of this lithium salt, determined using this 10% strength solution, is $2.5 \times 10^{-2}$ mole/liter.

As a guide, this critical micellar concentration is, under the same conditions, $2.4 \times 10^{-2}$ mole/liter for ammonium perfluorooctanoate $C_7F_{15}COO^-NH_4^+$, a commercial product used for the polymerization of certain fluorinated monomers.

EXAMPLE 4

68 g (0.41 mole) of pentafluorobutyl alcohol $C_2F_5CH_2CH_2OH$ were introduced into a 250-ml reactor, followed in the course of 15 minutes by 75.5 g (0.41 mole) of trichloroacetyl chloride. The mixture was heated to 60° C. for 30 minutes. After stripping with nitrogen, the product was distilled and 111.2 g of pentafluorobutyltrichloroacetate (b.p. 100° C. at 4000 Pa) were collected.

This ester was then photochlorinated at between 60° and 110° C. for 4 hours with 0.5 mole/h of chlorine, and then for 10–12 hours at 140°–145° C. with 0.3 mole/h of chlorine. 1 g of triethylamine hydrochloride was then added. The mixture was heated to 100° C. for 2 hours.

By distillation of the mixture with 13 effective plates, the following three fractions were obtained:

49 g at 108° C. at 96.4 kPa: fraction consisting of crude 2,2-(dichloro)pentafluoro-butanoyl chloride ($C_2F_5CCl_2COCl$), 10 g of intermediate fraction, and 31 g at 110°–116° C. at 96.4 kPa: fraction consisting essentially of trichloroacetyl chloride.

The 2,2-(dichloro)pentafluorobutanoyl chloride was identified by:

$^{19}F$ NMR for $CF_3$—$CF_2$—$CCl_2$—$COCl$ $\delta$(ppm/TFA)= −1.9 34.5

$^{13}C$ NMR: $\delta$(ppm)=118.2 111.1 82.8 162.5

EXAMPLE 5

193.8 g (0.443 mole) of an industrial mixture of fluorinated alcohols of formula $C_nF_{2n+1}CH_2CH_2OH$ having the following composition:

| n | % |
|---|---|
| 6 | 49.3 |
| 8 | 30.5 |
| 10 | 13.5 |
| 12 | 5.7 |
| $\geq$14 | 1 | were introduced into the same apparatus as in Example 3-a.

After the addition of 120 g of trichloroacetyl chloride, the mixture was heated to 60° C. for 1 hour and was then stripped with nitrogen. The product was then photochlorinated for 6 hours at 120°–130° C. with 0.5 mole/h of chlorine, and then for 14 hours at 150° C. with 0.2 mole/h of chlorine. The acidity liberated is assayed in the gaseous outflow.

3 g of triethylamine hydrochloride were then added. The mixture was maintained at 100° C. for 2 hours before being vacuum distilled to separate the following fractions:

1st fraction (40° C. at 4933 Pa): trichloroacetyl chloride,

2nd fraction (from 62° C. at 3333 Pa to 155° C. at 2400 Pa): 216 g of a crude mixture of the chlorides of formulae: $C_nF_{2n+1}CCl_2COCl$ (total chlorine: 24.9%)

residue: 28 g.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. Functional chlorofluoro compound, comprising the general formula:

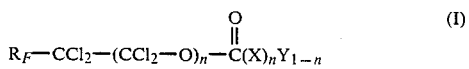

in which $R_F$ denotes a perfluoroalkyl radical, n is equal to 0 or 1, X denotes a chlorine or fluorine atom or a trichloromethyl or trifluoromethyl radical, and Y denotes a chlorine atom, an optionally salified or esterified hydroxyl group or an optionally mono- or di-substituted amino group, the arrangement $R_F$—$CCl_2$—$(CCl_2$—$O)_n$ containing at least 3 carbon atoms.

2. The compounds according to claim 1, wherein $R_F$ is a linear radical containing from 2 to 12 carbon atoms.

3. The compound according to claim 1, wherein X is a trichloromethyl radical.

4. The compound according to claim 1, wherein Y is a hydroxyl group salified with an inorganic base, ammonia or a primary, secondary or tertiary amine.

5. The compound according to claim 1, wherein Y is a hydroxyl group esterified with an aliphatic or cycloaliphatic alcohol.

6. The compound according to claim 1, wherein Y is an amino group unsubstituted or substituted with alkyl, cycloalkyl, aromatic or heterocyclic radicals.

7. Process for preparing the compounds of formula:

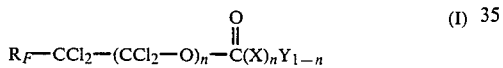

in which $R_F$ and X are defined in claim 1, comprising photochlorinating an ester of formula:

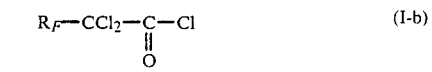

8. Process for preparing the compounds of formula:

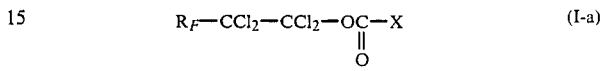

in which $R_F$ is as defined in claim 1, comprising heating a compound of formula:

$$R_F-CCl_2-CCl_2-OC-X \quad \text{(I-a)}$$
$$\phantom{R_F-CCl_2-CCl_2-O}\|\phantom{X}$$
$$\phantom{R_F-CCl_2-CCl_2-O}O$$

to a temperature ranging from 60° to 140° C.

9. The process of claim 8, where the temperature is between 80° and 120° C.

10. The process according to claim 8, wherein the reaction is carried out in the presence of a tertiary amine or a salt of such an amine.

11. The process according to claim 8, wherein a crude compound (I-a), as obtained by photochlorination of formula:

$$R_F-CCl_2-CCl_2-OC-X \quad \text{(I-a)}$$
$$\phantom{R_F-CCl_2-CCl_2-O}\|\phantom{X}$$
$$\phantom{R_F-CCl_2-CCl_2-O}O$$

in which $R_F$ and X are defined in claim 1, comprising photochlorinating an ester of formula:

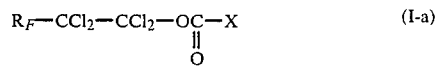

is used.

* * * * *